United States Patent [19]

Sibley et al.

[11] 4,374,745

[45] Feb. 22, 1983

[54] CLEANING COMPOSITIONS

[75] Inventors: Murray J. Sibley, Berkley; Rebecca F. Nite, Cupertino, both of Calif.

[73] Assignee: Barnes-Hind Pharmaceuticals, Inc., Sunnyvale, Calif.

[21] Appl. No.: 292,752

[22] Filed: Aug. 13, 1981

[51] Int. Cl.$^3$ .................... C11D 1/68; C11D 3/20
[52] U.S. Cl. .................... 252/106; 252/162; 252/173; 252/174.15; 252/174.21; 252/174.24; 252/DIG. 10; 252/170; 106/13; 427/140; 156/94
[58] Field of Search ........ 252/DIG. 10, 70, 89.1, 252/162, 170, 173, 174.15, 174.21, 174.22, 174.23, 174.24, 106; 106/13; 427/140; 156/94

[56] References Cited

U.S. PATENT DOCUMENTS

| | | | |
|---|---|---|---|
| 2,370,565 | 10/1940 | Muskat et al. | 260/78 |
| 3,249,550 | 5/1966 | Metters | 252/161 |
| 3,884,826 | 5/1975 | Phares, Jr. et al. | 252/106 |
| 4,046,706 | 9/1977 | Krezanoski | 252/106 |

FOREIGN PATENT DOCUMENTS 6092901  7/1981  Japan .

*Primary Examiner*—John E. Kittle
*Assistant Examiner*—Robert A. Wax

[57] ABSTRACT

An aqueous or gel cleaning composition is provided which comprises approximately by weight (a) 0.02 to 25.0% of at least one nonionic cleaner; (b) 0.01 to 10% of a diglycol carbonate monomer; (c) 0.01–10.0% of an antifog agent; (d) up to 25% of a lower aliphatic alcohol; (e) up to 1.0% of a preservative agent; (f) the balance water and if a gel is desired 0.1 to 5.0% of a thixotropic gelling agent.

14 Claims, No Drawings

CLEANING COMPOSITIONS

BACKGROUND OF THE INVENTION

(1) Field of the Invention

This invention relates to cleaning compositions. More particularly, this invention relates to cleaning compositions in either aqueous solution or gel form, which are especially suitable for cleaning and treating glass and plastic lenses and eyeglass frames.

(2) The Prior Art

Both glass and plastic spectacle lenses as well as their frames collect a variety of soil deposits during daily wear. These include skin oils, perspiration, dust, dirt, lint, makeup, environmental soils, hairspray, and the like, which may reduce visual acuity, cosmetic appearance and comfort. In addition, some of these soils can stain both plastic and metal eyeglass frames.

Another common problem is the fogging of lenses due to temperature changes around the spectacle, e.g., moving from warmer to colder environments or perspiration around the eyes and nose area. Thus, a desirable component in a lens cleaner is to include a component having an antifogging property. One such example of an antifogging cleaner is U.S. Pat. No. 3,939,090.

Static charges can also be a problem since these charges attract dust particles. Thus, including a component having an antistatic property is desirable.

A common problem both with glass and plastic spectacle lenses is the appearance of hairline scratches. This is disfiguring to the lenses, detrimental to the cosmetic appearance of the lenses and can eventually lead to reduction in visual acuity.

One embodiment of this invention provides that the cleaner be in a gel form. Gel cleaners have been described in the past and one such cleaner for hard contact lenses is described in U.S. Pat. No. 3,884,826.

SUMMARY OF THE INVENTION

This invention comprises combinations of chemical agents which provide; (1) outstanding cleaning of all commonly-encountered eyeglass lens and frame soilants, (2) coats the lenses and frames with a uniform film which is antifog and antistatic, (3) includes an agent which fills hairline scratches in lenses. Formulas are described which are either solutions or thixotropic gels which provide the desirable properties.

It is thus the general object of this invention to provide a cleaning composition suitable for cleaning lenses and for filling hairline scratches in lenses and having an antifogging compound.

Another object of this invention is to provide a lens cleaner suitable for both plastic and glass lenses.

Yet another object of this invention is to provide a lens cleaner in the form of a solution or a gel.

An even further object of this invention is to provide compositions for cleaning eyeglass frames.

Other object features and advantages of the present invention will be evident from the following detailed description of the invention.

DETAILED DESCRIPTION OF THE PREFERRED EMBODIMENTS

In the broadest form, the cleaning compositions of the present invention include the provisions of an aqueous composition comprising, approximately by weight;

(a) from 0.02 to 25.0% of at least one nonionic cleaner, (b) from 0.01 to 10.0% of a diglycol carbonate monomer;

(c) from 0.01–10.0% of an anti-fog agent, (d) up to 25% of a lower aliphatic alcohol, (e) up to 1.0% of a preservative agent, and the balance water.

The cleaning agents used in the compositions of this invention are nonionic cleaners. A single cleaner of the first class described may be used or it may be combined with a nonionic cleaner of the second class. In either case the total amount of nonionic cleaner is present in an amount by weight from about 0.02% to about 25.0%, preferably from about 0.5% to about 5.0% by weight of the total composition.

The nonionic cleaner of the first class which may be used includes the polyoxyethylene fatty acids esters and alcohol ethers sold under the trade names of Tweens, Spans, Myrij and Brij; oxyethylene oxypropylene polymers (Pluronics) and alkylaryl oxyethylene polymers (Triton or Igepal ®). Of particular utility are the Igepal ® CA surfactants (available from GAF Corporation), which are derived from octylphenol and ethylene oxide. This nonionic cleaner, which also serves as an antistatic agent, is used in an amount from 0.01% to 20% by weight, preferably about 0.5% to 5.0% by weight.

A second class of nonionic cleaners which is used, preferably in combination with the first described cleaner, is an organosilicone, such as a water soluble, polyoxyalkylene or higher alkyl modifications of dimethyl polysiloxanes. In particular, the organo-modified silicone, L-720, sold by Union Carbide is preferred. When this nonionic cleaner is used the amount used is from 0.01% to 5.0% by weight of the total composition.

As indicated, one of the objects of this invention is to eliminate hairline scratches in lenses. Another component of the composition is a diglycol carbonate monomer such as diethylene glycol bis (allyl carbonate). This monomer is a colorless, liquid organic ester of low volatility, sold as CR-39 ® by P.P.G. Industries. The monomer is used in an amount from 0.01% to 10.0% by weight, preferably about 0.1% to about 1.0% by weight.

The next component in the cleaning composition is an anti-fogging/anti-static agent. Suitable agents include an organo-modified silicone. More specifically, a polyoxyalkylene or higher alkyl modifications or dimethylpolysiloxanes (Union Carbide L-77) or nonionic water soluble silicone glycol copolymers (Dow Corning ® 470A or 193 may be used). The antifogging agent is used in an amount from about 0.01% to about 10.0% by weight, preferably 0.1% to 5.0%.

The alcoholic component of the invention comprises any lower aliphatic alcohol having from 1 to 6 carbon atoms, such as the monohydric alkanols, i.e., methyl, ethyl, propyl, isopropyl, butyl, solbutyl, secturyl, hexyl and the like. The function of the alcohol is believed to be that of a solvent. The amount of alcoholic component employed is up to about 25.0% by weight, preferably from about 1.0% to about 20.0%.

The cleaning agent of the present invention is not intended for use in the eye, and thus, it is not designed to be a sterile product. However, it is ordinarily preferred to include a preservative so that should the cleaning agent become contaminated, it would resterilize itself. For this purpose the organic mercury compounds such as thimerosal and phenylmercuric acetate, and other sterilizing agents such as methyl paraben, propyl paraben, phenylethyl alcohol and chlorobutanol are entirely suitable for this purpose. Concentrations of from about 0.0001% to 1.0% may be employed if it is desired to use a preservative.

The balance of the composition in order to bring the same up to 100% will generally be water.

In another embodiment the cleaning formulation is provided in the form of a thixotropic gel. The solution formula above may have added thereto a gelling agent in an amount from 0.1% to 5.0% by weight agent. The gelling agent is used in sufficient amount to render the cleaner thixotropic and to give a suitable viscosity. A suitable viscosity range has been found to be 15,000 to 70,000 cps and it is preferred that the viscosity be about 30,000 to 50,000 cps (Brookfield RVF microviscometer spindle 6 at 20 RPM at 25° C.). If the product is too fluid, it will usually run off the lens before wiping and would be wasteful, since it would be difficult for the user to regulate the amount being dispensed from the container. On the other hand, too stiff a gel is not easily spread on the lens surface and might be tacky and not easily wiped.

Suitable gelling agents useful in the present invention are carboxypolymethenes, high molecular weight carboxy vinyl polymers, sold under the trade name Carbopol by G. F. Goodrich Company. Concentrations of from 0.1% to 5.0% by weight provide a suitable viscosity as defined above, but preferably 0.5% to 2.0%. Other typical thixotropic gelling agents, including inorganic clays, are hectorite (sold under such names as Ben-a-Gel and Macaloid), montmorillonite (bentonite), synthetic hectorite (such as that sold under the name of Laponite), and combinations of these such as hectorite with montmorillonite (sold under the name of Veegum), and hectorite with a hydrocolloid such as hydroxyethylcellulose (sold under the name Bentone). Other examples of thixotropic gelling agents are the colloidal or fibrous aluminas such as sold under the trade names of Dispal, Alon and Baymal.

To make the gel formulations it is necessary to first mix the gelling agent with the nonionic cleaner and antifogging agent in the water phase. The carbonate monomer is then solubilized in the alcohol and the two phases are combined. The pH of the combined phases is adjusted to about pH 6.0 to 8.0, preferably about pH 7.0 with sodium hydroxide to neutralize the gel.

The cleaning compositions described above possess the following characteristics; excellent cleaning, antifog coating, antistatic performance, disguise hairline scratches and have a low residue. It is to be understood that the compositions work equally well on both plastic and glass spectacle lenses.

The following examples merely serve to illustrate the invention in more specific detail, and when read in conjunction with the foregoing description, will aid in determining the full scope of the present invention. The examples are merely illustrative and not intended to restrict the invention. All parts, proportions and ratios in the following examples as well as in the appended claims are by weight unless otherwise indicated.

EXAMPLE I

A lens cleaning solution was formulated by mixing the following:

| Component | Function | Amount (%, by weight) |
|---|---|---|
| Oxyethylene polymer[1] | Cleaner | 1.0 |
| Diglycol carbonate[2] | Scratch filler | 0.2 |
| Silicone glycol copolymer[3] | Antifogger | 1.0 |
| Ethanol | Solvent | 10.0 |
| Thimerosal | Preservative | 0.0004 |
| Purified water | | q.s. to 100% |

[1] Igepal ® CA-630 from GAF Corporation
[2] CR-39 ® from P.P.G. Industries
[3] Silicone 193 from Dow-Corning This formulation was tested by eyeglass wearers and was found to provide all of the desirable properties described above. In addition, the formula was easy to apply, non greasy, did not leave undesirable residues and are long-lasting in effect.

EXAMPLE II

A lens cleaning gel was formulated by mixing the following:

| Component | Function | Amount (%, by weight) |
|---|---|---|
| Carboxyvinyl polymer[1] | Gelling Agent | 0.5 |
| Oxyethylene polymer[2] | Cleaner | 1.0 |
| Organosilicone[3] | Cleaner | 0.1 |
| Diglycol Carbonate[4] | Scratch filler | 0.2 |
| Dimethylpolysiloxane[5] | Antifogger | 1.0 |
| Ethanol | Solvent | 10.0 |
| Thimerosal | Preservative | 0.004 |
| Sodium, Hydroxide, 1N | Neutralizer | q.s. to pH 7.0 |
| Purified Water | | q.s. to 100% |

[1] Carbopol ® 940 from B.F. Goodrich.
[2] Igepal ® 6CA-630 from GAF Corporation.
[3] L-720 from Union Carbide Corporation.
[4] CR-39 ® from P.P.G. Industries.
[5] L-77 from Union Carbide Corporation This formulation was tested by eyeglass wearers and was found to provide all of the desirable properties described above. In addition, the formula was easy to apply, non-greasy, did not leave undesirable residues and are long-lasting in effect.

While the invention has been described and illustrated herein by references to various specific materials, procedures and examples, it is understood that the invention is not restricted to the particular materials and procedures selected for that purpose. Numerous variations of such details can be employed, as will be appreciated by those skilled in the art.

What is claimed is:

1. An aqueous composition for cleaning lenses and spectacle frames comprising:
   (a) from 0.02 to 25.0% by weight of at least one nonionic cleaner;
   (b) from 0.01 to 10.0% by weight of a diglycol carbonate monomer;
   (c) from 0.01–10.0% by weight of an anti-fogging agent;
   (d) up to about 25% by weight of a lower aliphatic alcohol;
   (e) up to 1.0% by weight of a preservative agent; and
   (f) water.

2. The composition according to claim 1, wherein said nonionic cleaner is a mixture of an alkylaryl oxyethylene polymer in an amount from 0.01 to 20% by weight, and an organosilicone in an amount from 0.01% to 5.0% by weight.

3. The composition according to claim 1 or 2, wherein said nonionic cleaner is present in an amount from 0.5% to 5.0% by weight.

4. The composition according to claim 1, wherein the alcohol is ethyl alcohol and is present in an amount from 1.0% to 20% by weight.

5. The composition according to claim 1, wherein said antifogging agent is present in an amount from 0.1% to 5.0% by weight and is selected from the group consisting of alkyl modified dimethyl polysiloxanes and water soluble silicone glycol copolymers.

6. The composition according to claim 1, wherein said preservative agent is thimerosal and is present in an amount from 0.0001% to 1.0% by weight.

7. A gel composition for cleaning lenses and spectacle frames comprising:
(a) from 0.02 to 25.0% by weight of at least one nonionic cleaner;
(b) from 0.01 to 10.0% by weight of a diglycol carbonate monomer;
(c) from 0.01–10.0% by weight of an anti-fogging agent;
(d) from 0.1 to 5.0% by weight of a thixotropic gelling agent in an amount sufficient to form a gel;
(e) up to about 25% by weight of a lower aliphatic alcohol;
(f) up to 1.0% by weight of a preservative agent; and
(g) water.

8. The composition according to claim 7, wherein said nonionic cleaner is a mixture of an alkylaryl oxyethylene polymer in an amount from 0.01 to 20% by weight, and an organosilicone in an amount from 0.01% to 5.0% by weight.

9. The composition according to claims 7 or 8, wherein said nonionic cleaner is present in an amount from 0.5% to 5.0% by weight.

10. The composition according to claim 7, wherein the alcohol is ethyl alcohol and is present in an amount from 1.0% to 20% by weight.

11. The composition according to claim 7, wherein said antifogging agent is present in an amount from 0.1% to 5.0% by weight and is selected from the group consisting of alkyl modified dimethyl polysiloxanes and water soluble silicone glycol copolymers.

12. The composition according to claim 7, wherein said preservative agent is thimerosal and is present in an amount from 0.0001% to 1.0%.

13. The composition according to claim 7, wherein said gelling agent is a high molecular weight carboxy vinyl polymer and is present in an amount from 0.5% to 2.0% by weight.

14. The composition according to claim 7, wherein said composition has a viscosity of 15,000 to 70,000 cps at 25° C.

* * * * *